United States Patent [19]

Vassiliadis et al.

[11] Patent Number: 5,123,845

[45] Date of Patent: Jun. 23, 1992

[54] DENTAL LASER ASSEMBLY

[75] Inventors: Arthur Vassiliadis; Joseph W. Shaffer, both of Mountain View; David J. Fullmer, Foster City; Michael H. Brewer, Felton; David R. Hennings, Newcastle, all of Calif.; Terry D. Myers, Farmington Hills, Mich.

[73] Assignee: American Dental Laser, Inc., Troy, Mich.

[21] Appl. No.: 707,162

[22] Filed: May 28, 1991

Related U.S. Application Data

[60] Division of Ser. No. 493,965, Mar. 15, 1990, Pat. No. 5,055,048, which is a continuation-in-part of Ser. No. 342,190, Apr. 24, 1989, Pat. No. 4,940,411, which is a continuation-in-part of Ser. No. 236,450, Aug. 25, 1988, abandoned.

[51] Int. Cl.$^5$ ................................................ A61C 5/00
[52] U.S. Cl. ................................................... 433/215
[58] Field of Search ................... 433/215, 216; 606/3, 606/15, 16, 10

[56] References Cited

U.S. PATENT DOCUMENTS

| | | | |
|---|---|---|---|
| 4,784,135 | 11/1988 | Blum et al. | 606/3 |
| 4,852,567 | 8/1989 | Sinofsky | 128/303.1 |
| 4,874,315 | 10/1989 | Featherstone et al. | 433/215 |
| 4,925,523 | 5/1990 | Braren et al. | 156/643 |
| 5,020,995 | 6/1991 | Levy | 433/215 |

OTHER PUBLICATIONS

"Heatless Laser Etching", *Popular Science*, Dec. 1983, p. 114.

*Primary Examiner*—Cary E. O'Connor
*Attorney, Agent, or Firm*—Gifford, Groh, Sprinkle, Patmore and Anderson

[57] ABSTRACT

A dental laser assembly is disclosed for use in eradicating carious lesions in teeth, the treatment of sensitive teeth, as well as the removal of soft tissue, the incising of the frenum, opurculum, anesthesia of the tooth, etching enamel for restorations or orthodontic appliance fixation, the welding of fixed prosthesis, removal of bacterial flora periodontal pockets, removal and/or vaporization of healthy or necrotic pulp, the vertical and/or horizontal condensation of gutta percha or any other root canal sealant, the cauterization of blood vessels in the oral cavity, vaporizing bone tissue, removing tartar, apical fusion of foramina, enlarging and shaping root canal, removing carbon from surface of teeth, removal of enamel, bleaching teeth, etching dentin, separating orthodontic brackets, merging hydroxyapatite to bone and enamel, amalgam removal and undercutting of carious and/or healthy dentin and/or cementum. The laser assembly includes a housing having a cavity in which a pulsed laser is contained. The laser is excited so that the laser emits a laser beam along a predetermined axis that is in line with a fiber optic delivery system and at a pulse rate of one to 10,000 pulses per second and an average power variable from one tenth to 50 watts. A handpiece is dimensioned to be inserted into a human mouth while an optical fiber optically connects the laser output to the handpiece. The laser assembly also includes a continuous output aiming laser which, upon activation, provides a continuous laser aiming beam coaxial to the treatment beam. Both beams are then introduced into a fiber optic delivery system.

12 Claims, 4 Drawing Sheets

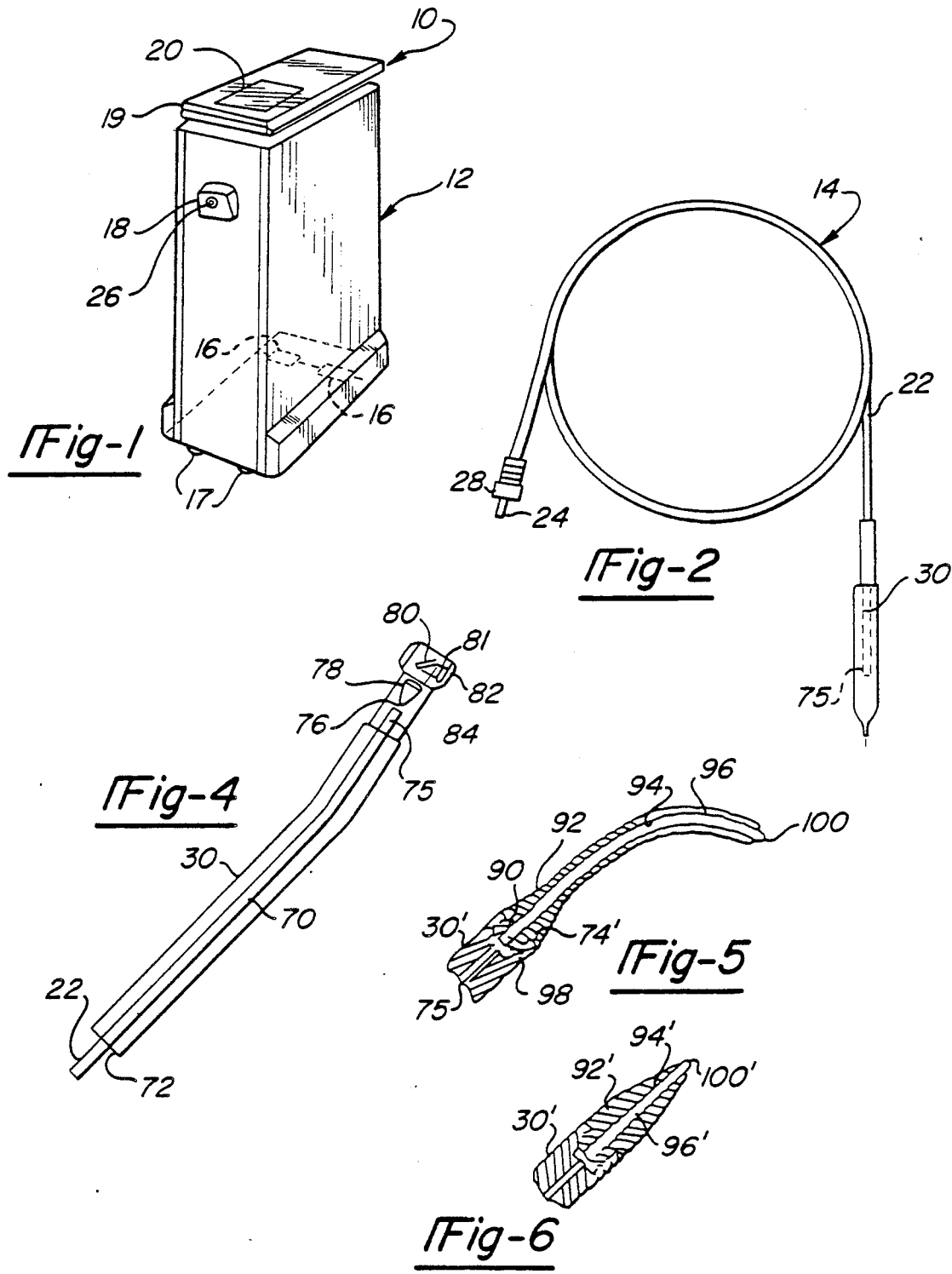

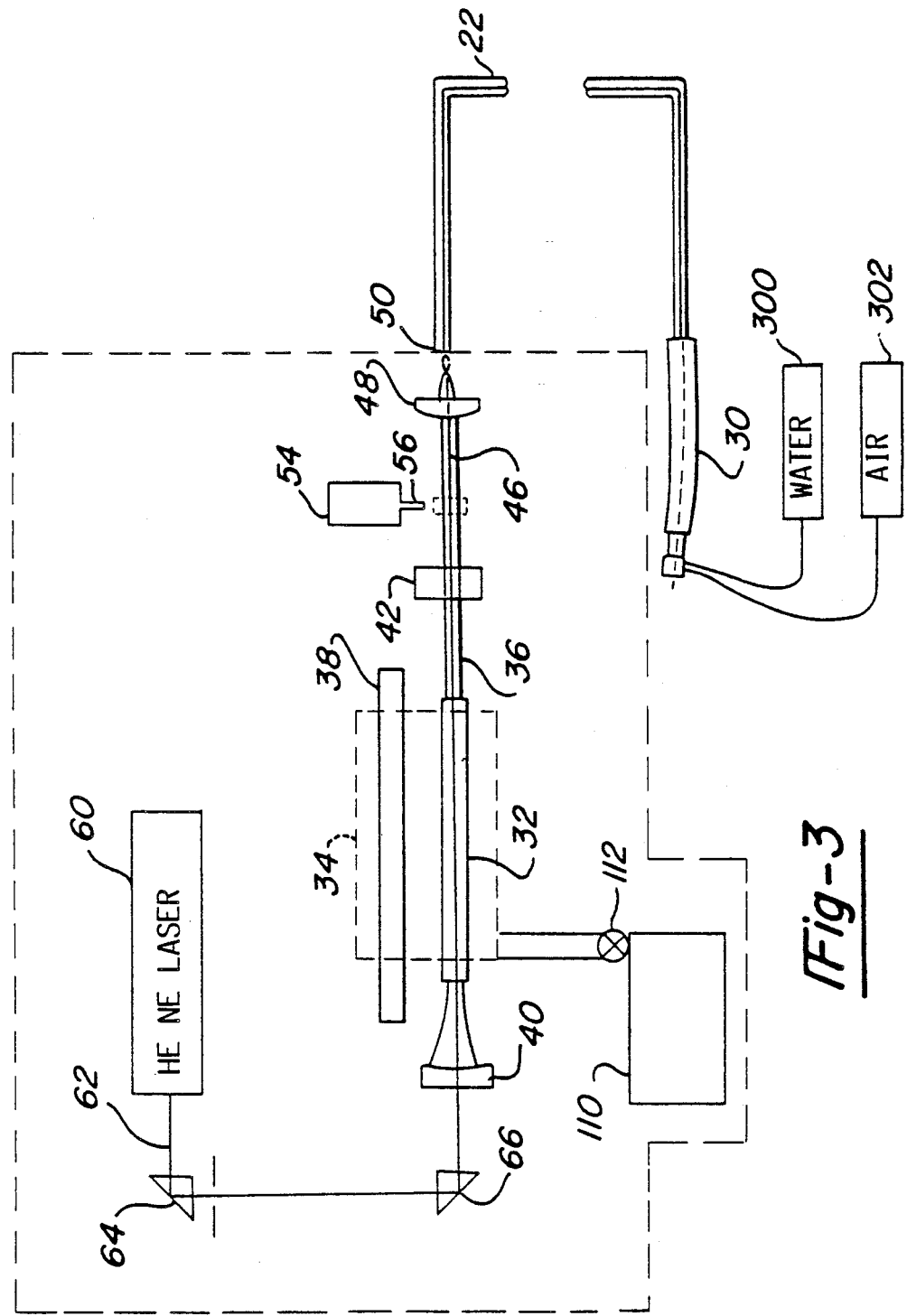

DENTAL LASER ASSEMBLY

CROSS REFERENCE TO RELATED APPLICATIONS

This is a divisional of copending application Ser. No. 07/493,965 filed on Mar. 15, 1990, now U.S. Pat. No. 5,055,048, which is a continuation-in-part of U.S. patent application Ser. No. 342,190, entitled DENTAL LASER ASSEMBLY, filed on Apr. 24, 1989, now U.S. Pat. No. 4,940,411, which is a continuation-in-part of U.S. patent application Ser. No. 236,450, entitled DENTAL LASER ASSEMBLY, filed on Aug. 25, 1988, abandoned.

BACKGROUND OF THE INVENTION

I. Field of the Invention

The present invention relates generally to laser assemblies and, more particularly, to a laser assembly particularly suited for dental applications such as the eradication of carious lesions, the treatment of sensitive teeth, and the removal of soft tissue.

II. Description of the Prior Art

There have been a number of previously known Neodymium doped Yttrium Aluminum Garnet (Nd:YAG) laser systems that have been used for medical surgical applications. These previously known laser systems typically have been constructed to provide very high average powers, i.e. in the range of 60 to 100 watts of continuous power. Consequently, these previously known systems have required high power electrical supply systems, typically 220 volts.

There have been a number of disadvantages to these previously known Nd:YAG systems. One disadvantage is that these systems are heavy and difficult to move and also require substantial cooling systems in order to cool the laser head and the power supply. Furthermore, since such systems are typically powered by 220 volt line current, it has been necessary to install separate electrical receptacles for these previously known systems.

These previously known systems oftentimes use fiber optic delivery having a simple focusing lens at the output from the fiber optic. In some systems, contact tips were used to deliver the laser power to the target site. These previously known delivery systems, however, had been somewhat bulky and difficult to use.

To date, there has never been a Nd:YAG laser system particularly suited for dental laser applications. Such applications include the eradication of carious lesions, the treatment of sensitive teeth, as well as the removal of soft tissue.

U.S. Pat. No. 4,818,230 to Myers et al. is commonly owned with this patent and discloses a method for removing decay from teeth. In the Myers' patent, the power levels of the laser was limited to 100 millijoules per pulse for fear of causing pain for the patient by heating the tooth. New research and new applicatons, however, have made it necessary to consider higher powers and pulse repetition rates.

SUMMARY OF THE PRESENT INVENTION

The present invention provides a dental laser assembly which overcomes all of the above mentioned disadvantages of the previously known devices.

In brief, the dental laser assembly of the present invention comprises a housing having a cavity in which a pulsed Nd:YAG laser is contained. An exciting flash lamp is also contained within the cavity and, upon excitation, causes the laser to emit a pulsed laser beam along a predetermined axis. Preferably, the repetition rate for the laser is approximately one to 10,000 pulses per second and a duration at each pulse between several picoseconds and several milliseconds. The average power of the laser is between one tenth and 50 watts and is adjustable.

An optical fiber is connected through a coupling to the housing so that the axis of the optical fiber is coincidental with the axis of the laser beam output. The other end of the fiber optic is connected to an elongated handpiece. This handpiece preferably includes either a mirror assembly or an arcuate fiber optic segment or ceramic tip so that the handpiece directs the laser beam in a direction substantially perpendicular to the axis of the handpiece. This allows the handpiece to be inserted and manipulated into the mouth of the patient and used in the fashion of a conventional dentist drill.

In addition, the laser assembly of the present invention comprises a continuous wave, low powered visible laser having its output coaxial with the output from the pulsed laser. The continuous wave laser is preferably a helium-neon (HeNe) laser so that its output is in the visible range of the human eye. The continuous wave laser thus provides an aiming beam for the laser since the output from the Nd:YAG laser is invisible.

In operation, upon excitation of the pulsed laser, the pulse laser generates an output capable of removing carious lesions, the treatment of sensitive teeth, as well as removing soft tissue. Furthermore, the optical segment on the handpiece is preferably removable for cleaning and sterilization and replaceable with different optical segments for different dental applications.

It has also been found that, by using relatively low laser powers, i.e. 30–300 millijoules per pulse, and lasing healthy dentin and/or enamel, desensitation of the tooth is achieved. It has been found that by irradiating surface areas of the tooth, analgesia can be applied to the tooth thereby causing an anesthesia effect upon the tooth. This in turn permits higher energy levels per pulse to be utilized without causing patient discomfort which, in turn, allows the dental procedure to be quickly accomplished.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a view illustrating the main unit of a preferred embodiment of the laser assembly of the present invention:

FIG. 2 is a view illustrating the delivery system for the preferred embodiment of the invention:

FIG. 3 is a diagrammatic view illustrating the preferred embodiment of the present invention:

FIG. 4 is a side sectional view illustrating a preferred handpiece of the present invention:

FIG. 5 is a fragmentary sectional view similar to FIG. 4 but illustrating a different tip;

FIG. 6 is a view similar to FIG. 4 but illustrating still another further modification thereof:

DETAILED DESCRIPTION OF PREFERRED EMBODIMENTS OF THE PRESENT INVENTION

Figure 7:
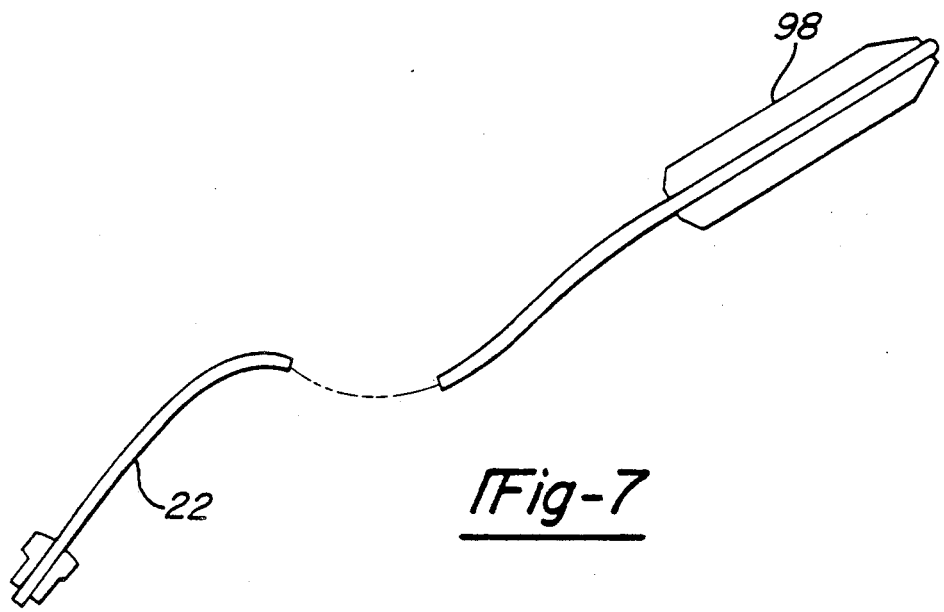
FIG. 7 is a sectional view of an alternative embodiment of the cable and handpiece.

With reference first to FIGS. 1 and 2, a preferred embodiment of the dental laser assembly 10 of the present invention is thereshown and comprises a main unit 12 and the fiber optic laser beam delivery system 14. The main unit 12 preferably includes rollers 16 at one end for mobility so that the main unit 12 can be moved as desired. The other end of the main unit rests on posts 17. The unit is lifted with a retractable handle 19 so as to be moved on the rollers 16.

Still referring to FIGS. 1 and 2, the main unit 12 includes a fiber optic output connector 26 along one side. A control panel 20 is provided at the top of the main unit 12 to control the activation and use of the dental laser system 10.

Referring still to FIGS. 1 and 2, the fiber optic cable assembly comprises an elongated fiber optic 22 which is flexible. One end 24 of the fiber optic 22 is received within the fiber optic connector 26. A lock nut 28 adjacent the end 24 of the fiber optic 22 locks to the connector 18 in order to secure the fiber optic 22 to the main unit 12 for a reason to be subsequently described.

Referring now particularly to FIG. 2, a handpiece 30 is provided at the opposite end 75 of the fiber optic cable 22. As will be subsequently described in greater detail, the fiber optic cable 22 delivers a laser beam from the end 24 to the handpiece 30.

With reference particularly to FIG. 3, an Nd:YAG laser 32 is contained within a cavity 34 in the main unit 12. The YAG laser 32 is positioned within the cavity 34 so that the laser 32 generates a laser output beam along a predetermined axis 36. Any conventional means, such as a flash lamp 38, is also contained within the cavity 34 to excite the laser 32 so that the laser 32 generates a pulsed output.

The YAG laser has a pulse laser repetition rate of between one and 10,000 pulses/sec., an average power of up to 50 watts and preferably between one tenth and fifty watts, a pulse duration of between a picosecond and several milliseconds and a peak energy of up to five joules/pulse. The peak power will vary depending upon the pulse duration and pulse energy and, similarly, the average power will vary depending upon the energy of each pulse, and the repetition rate. However, since the output power of the laser is less than 50 watts, the laser can be operated from a standard 110 volt electrical power supply and without the necessity of an external cooling system to cool the laser cavity 34.

Conventional electronics operated through the control panel 20 enable the average power, pulse energy, and pulse repetition rate to be user selected. These factors will vary in dependence upon the dental procedure involved as subsequently discussed.

Still referring to FIG. 3, a reflecting mirror 40 is positioned adjacent one end of the laser 32 while a semi-reflective mirror 42 is positioned adjacent the other end of the laser 32. The mirrors 40 and 42 thus cause the laser 32 to generate an output along the axis 46, through a fiber focus lens 48 and into one end 50 of the fiber optic 22. The fiber optic 22 then carries or delivers the laser output from the laser 32 to the handpiece 30 which will be subsequently described in greater detail.

A shutter solenoid 54 is also preferably contained within the main housing 12 and operates a movable shutter 56 (illustrated only diagrammatically). With the shutter 56 in its upper of retracted position, illustrated in solid line, the laser beam from the laser 32 passes through the lens 48 and out through the fiber optic 22. conversely, with the shutter 56 in its extended position, illustrated in phantom line, the shutter 56 blocks the output from the laser 32 to prevent unintended laser outputs from the handpiece 30.

Still referring to FIG. 3, the main unit 12 also includes a continuous wave laser 60, such as a helium-neon (HeNe) laser. Such a laser provides a very low power output but, unlike the Nd:YAG laser 23, the output from the helium-neon laser 60 is in the visible range.

The output 62 from the HeNe laser 60 is reflected by prisms 64 and 66 through the mirror 40 so that the HeNe laser output 62 is coaxial with the axis 36 and thus with the laser outputs from the Nd:YAG laser 32. Thus, both the laser output from the continuous laser 60 as well as the pulse laser 32 are delivered through the fiber optic cable 22 to the handpiece 30. The continuous laser output 62 provides an aiming output since the output from the pulse laser 32 is invisible.

Other means for aiming the pulsed laser can, of course, be alternatively used.

The main housing further includes a cooling system 110 for cooling pulsed laser 32. The cooling system can be of any conventional construction, for example, having a coolant of 50% ethylene glycol and 50% deionized water. This coolant is pumped by a pump while a flowmeter 112 monitors the flow of the coolant. The fluid is pumped through the laser cavity and through a radiator and then circulated. In the event that the flow of the coolant is interrupted, the laser 32 is deactivated in order to prevent the laser 32 from overheating.

Alternatively, the cooling system 110 is housed separately from the main housing. Such an arrangement is advantageous in that it (1) minimizes the size of the housing and (2) allows the cooling system 110 to be combined with the cooling systems for other equipment used by the dentist.

With reference now particularly to FIG. 4, one preferred embodiment of the handpiece 30 is thereshown and comprises an elongated body 70 having a first end 72 and a second end 74. The fiber optic cable 22 extends through the handpiece body 70 from the end 72 and terminataes at a point 76 short of the handpiece end 74. The output from the end 75 of the fiber optic is concentrated by a collimating lens 78 to a mirror 80. The mirror 80 reflects the laser output substantially at a right angle to the axis of the handpiece body 70, through a lens 81 and a protective window 82 and so that the laser output focuses at a point 84 adjacent to the output window 82 of the handpiece body 70.

Preferably, the handpiece 30 is of substantially the same shape and size as a conventional dentist drill. As such, the handpiece body 70 can be easily manipulated in the mouth of the patient in the same fashion as a dental drill.

In operation, upon activation of both lasers 60 and 32, both the continuous wave from the laser 60 as well as the pulsed output from the laser 32 are delivered through the fiber optic 22, through the collimating lens 78 (FIG. 4), mirror 80, focusing lens 81 and window 82 so that both lasers focus at the point 84. Since only the output from the continuous wave laser 60 is in the visible range, the laser beams can be easily focused since the size of the visible laser 60 is smallest at the point 84. When the laser is properly focused, activation of the pulse laser 32 removes the carious lesions, or the soft tissues as the case may be. Furthermore, the laser beam simultaneously sterilizes the work area during use which is particularly advantageous for the removal of soft tissue and dental decay.

The actual power and energy levels used by the operator or dentist will vary depending upon the desired dental procedure. It has been found, for example, that lasing the enamel of a healthy tooth with relatively low energy levels, e.g. less that 100 millijoules per pulse, densensitizes the tooth by temporarily sealing or otherwise deactivating the dentinal tubules which normally carry the pain signals of the tooth.

With the tooth desensitized, higher energy levels, i.e. energy levels between 100 millijoules and five joules per pulse, can be used without causing patient discomfort. Since higher energy levels per laser pulse eradicate more dental decay, disease, soft tissue and the like per pulse than laser pulses of lower energy, i.e. less than 100 millijoules/pulse, the overall dental procedure can be accomplished more quickly. This, in turn, saves "chair time" for the dentist and also is psychologically less stressful and less painful for the patient.

It has also been found that both temporary and permanent desensitization of the tooth can be more rapidly and effectively achieved by coating the tooth with a pigmented material prior to lasing. Darker materials, such as organic inks, have proven most effective for a Nd:YAG laser. However, different lasers are expected to react differently depending upon the optical characteristics of the laser.

The average power required for soft tissue procedures is higher than for tooth procedures, and requires higher pulse repetition rates. Accordingly, a variable pulse repetition rate is provided to provide a smoother output and a higher average power.

In most cases the laser achieves sterilization through eradication of bacteria. Complete sterilization, however, is not possible in all cases. Even in these cases where complete sterilization is not possible, reduction of bacteria and partial sterilization is almost always achieved.

It has also been found in laboratory experiments that bacteria are "scattered" during high laser repetition rates of the laser, i.e. repetition rates in excess of about 30 laser pulses/second. Furthermore, efficient removal of bacteria without bacteria scattering is achieved within a range of 15–25 laser pulses/second. It has been found that below 15 pulses/second eliminates scattering but unduly prolongs the sterilization process while some scattering occurs above 25 pulses/second and unacceptable scattering occurs above 30 pulses/second. A slower pulse rate would be available for use with the holmium YAG laser because it functions more at a surface level.

A pigment can also be sprayed on the tooth prior to lasing. This pigment spray enhances light absorption by the tooth.

It has also been found that lasing teeth may carbonize the outer layer of the tooth. Removal of this carbon can be easily achieved by treating the carbonized portion of the tooth with an oxihalogen, preferably a hypo chlorite such as diluted sodium hypo chlorite or other hypo chlorites or chlorides or using water, and then lasing the tooth.

External cooling of the tooth may also be necessary at high average power levels as well as at high energy/pulse levels and under most circumstances with the holmium YAG laser. Such tooth cooling can be accomplished in any conventional fashion, such as by spraying water on the tooth from a source 300 (FIG. 3). Since certain types of laser emissions are absorbed by water, a drying means 302, such as an air sprayer, is activated after each water spray but prior to a subsequent activation of the pulsed laser.

Figure 9:
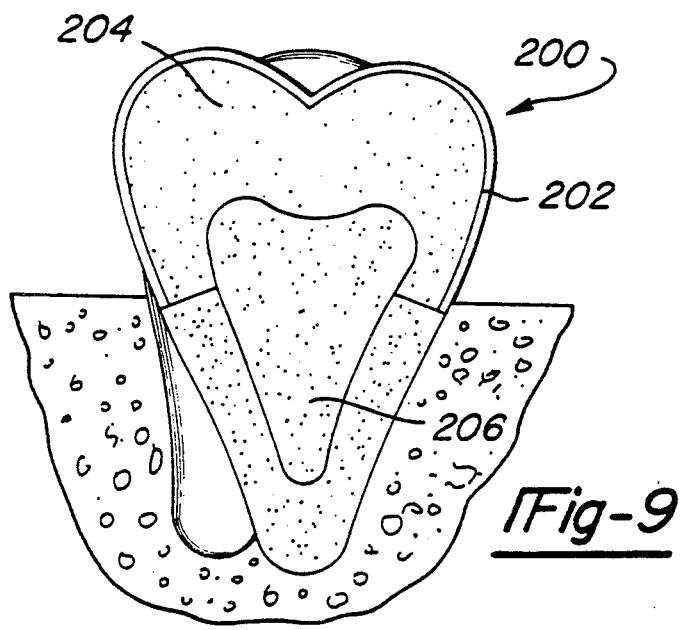
FIG. 9 is a crossectional view of a tooth.
Figure 10:
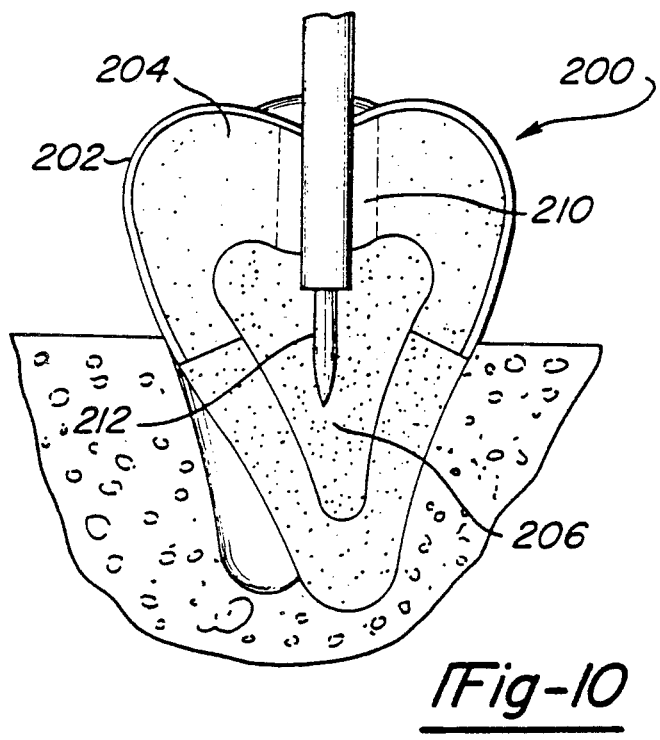
FIG. 10 is a crossectional view illustrating an endontic procedure.

It has also been found that high energy levels, i.e. energy levels between 100 millijoules/pulse and five joules/pulse, are useful for endontic procedures such as root canals, apicoectomies and pulpectomies on a tooth 200 shown in FIGS. 9 and 10. The tooth 200 has an enamel outer shell 202, dentin 204 and a pulp chamber 206. In such endontic procedures, the pulp chamber is opened at 210 (FIG. 10) and a laser tip 212 is inserted. Activation of the laser at high power and/or energy levels eradicates the soft tissue in the pulp chamber 206 as desired. Simultaneously, the laser sterilizes the pulp chamber 206 and prevents infection. Due to this sterilization, a partial pulpectomy, previously unknown, is possible without risk of infection of the pulp chamber. Furthermore, application of a pigmented material in the pulp chamber prior to lasing enhances the absorption of the laser emission along the root canal chamber. This enhanced absorption fuses the dentin and creates a smooth surface around the root canal which inhibits bacterial growth in the root canal chamber and accessory canals which typically are a host site for bacteria. As before, organic inks have proven most effective for this purpose.

The pigmented material, if desired, can be applied with a nozzle or manually.

It is well known that, in many cases, the tooth discolors following root canal surgery. Hydrogen peroxide has been previously used to bleach or whiten the discolored tooth. Lasing the tooth during application of the hydrogen peroxide causes the tooth bleaching to occur more rapidly and more completely. Additionally, suspension of the hydrogen peroxide in a gel or paste as it is applied to the tooth advantageously prevents the hydrogen peroxide from contacting and irritating the gum area.

These relatively high power and/or energy levels have also proven useful for performing curetage. Tumors and other growths can also be excised using such high powers.

Still other dental procedures are capable with the laser of the present invention. For example, it has been found that the laser of the present invention is advantageous for removing tartar buildup on the teeth. In such an application, the laser is focussed at the tartar and repeatedly activated until the tartar is removed.

The preferred embodiment of the laser of the present invention has also proven useful for apical fusion of foramina. In such an application, the laser is focussed at the tooth area surrounding the foramina and repeatedly activated until the area surrounding the foramina melts and fuses the foramina shut. This tooth material surrounding the foramina typically comprises healthy dentin.

The laser can also be used for shaping the canal during an endontic or root canal procedure. In such a procedure, the laser is aimed at the good or undiseased dentin surrounding the nerve canal in the tooth. The laser is then repeatedly activated thereby eradicating the dentin and shaping or enlarging the root canal as well as sterilizing the root canal.

The laser of the present invention can also be used to heat gutta percha in the cavity left by the removal of a carious lesion. This renders the gutta percha more fluid so that it flows deeper into crevices of the cavity and creates a better bond between the gutta percha and the cavity.

The laser of the present invention has also been used for the bloodless removal of soft tissue. In such an application, the laser is aimed at the soft tissue which is to be removed and repeatedly activated. During such a procedure, the laser beam simultaneously cuts the soft tissue and seals the blood vessels at the wound site as well as sterilizing the wound site. This in turn produces essentially a bloodless removal of the soft tissue.

The laser of the present invention can also be used for anesthetizing a tooth prior to preparation of the tooth with conventional instruments for removal of decay and/or propon material restoration. In such a procedure, the entire crown and/or root of the tooth is lased on all surfaces including, but not limited to, the buccal, lingual, and occlusal surfaces thereby anesthetizing the entire target tooth. Although the precise procedure in which laser analgesia of the tooth and nerve endings is unknown, it is believed that the laser beam acts to temporarily close the tubuals and depolarize the nerve cells of the odontablast layer of the pulp for a time period sufficient to permit the dental procedure to be performed. In either event, the laser penetrates the enamel, which may range up to 2> mm thick, in order to anesthetize the tooth temporarily.

The laser of the present invention can also be used for removing tooth enamel. Such removal is oftentimes necessary in order to eradicate diseased dentin behind the enamel. A holmium doped YAG laser has proven especially effective for the removal of enamel. An erbium doped YAG laser has also proven effective for enamel removal although, at present, erbium YAG lasers are more destructive to optical fibers of the type used in a dental delivery system than a holmium YAG laser. Furthermore, it has been found that cooling the tooth during enamel removal enables faster removal of the enamel without damaging the tooth. Such cooling can be accomplished by spraying a fluid, such as air or water, on the tooth during the enamel removal.

The laser can also be used for the intraoral welding of dental appliances, such as braces and bridges, in the mouth. Synthetic hydroxapatite can also be welded to the teeth to replace fillings by the laser.

The laser can be used to incise the upper or lower frenum both labial or lingual. The advantage is that with the laser this procedure may not be necessary and bleeding probably will not occur. A lower frenectomy is typically performed to cure a malady called "tongue tied".

The laser can also be used to remove amalgam.

The laser of this invention can also be used to etch the enamel prior to restoration with various types of composites. Under current therapy it is necessary prior to installing the restoration to seal the dentin with a material such as calcium hydroxide which acts as a thermal liner, rinse, dry, etch the enamel with phosphoric acid or a like agent, rinse, dry then restore. A substantial time and material benefit is realized with the laser in that all the above steps in a tooth restoration are unnecessary. The laser is passed over the intended etch surface of the enamel during the removal of decay or just prior to installation of the sealing or bonding material. These procedures are completed without anesthesia in most cases thereby creating a significant cost savings to the patient and/or doctor. The same procedure is used to etch enamel prior to bonding for brackets that fix to braces.

In the above discussed dental procedures, the laser has an energy output of between 0.1 millijoules per pulse and 5 joules per pulse, an average power of less than 50 watts and a pulse repetition rate of up to 10,000 pulses per second.

With reference now to FIG. 5, a modification of the handpiece is thereshown in which the end 74' of the handpiece body 30' includes an internally threaded bore 90. This bore 90 detachably receives an externally threaded tip 92. The tip 92 includes an elongated throughbore 94 in which an arcuate fiber optic segment 96 is contained. The fiber optic segment 96 is arranged in the tip 92 so that one end 98 is aligned with the end 75 of the fiber optic 22 so that the laser output from the fiber optic 22 passes through the fiber optic 96 to its external end 100. The external end 100 of the fiber optic segment 96 is preferably a contact point so that the laser output is focused at the end 100 of the fiber optic segment 96. Also, as shown in FIG. 5, the fiber optic segment 96 is preferably arcuate so that the contact end 100 is substantially at a right angle from the axis of the handpiece body 30'.

With reference now to FIG. 6, a modification of the tip 92 is thereshown in which the throughbore 94' is linear rather than arcuate as shown in FIG. 5. Consequently, the contact end 100' of the fiber optic segment 96' is aligned with the axis of the handpiece body 30'. In all other respects, however, the tip 92' shown in FIG. 6 is the same as the tip 92 shown in FIG. 5 and, for that reason, will not be again described.

With reference to FIG. 7, another embodiment of a delivery system is shown. This comprises a single fiber 22 throughout and from input to output ends. A simple handpiece 98 is used to hold the fiber for use in the mouth.

Figure 8:
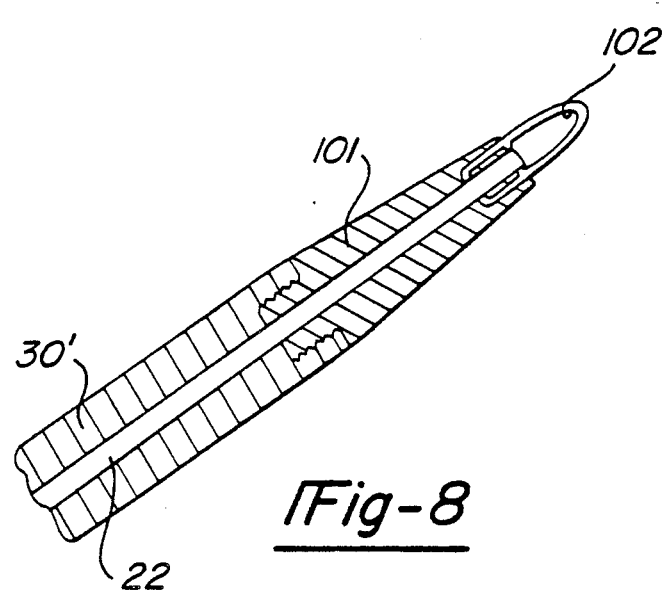
FIG. 8 is a fragmentary sectional view similar to FIG. 6 showing a further alternative embodiment of the tip.

With reference to FIG. 8, another embodiment of a tip 101 is shown that is designed to fit on the body 30'. The tip 101 is made of a ceramic material that acts as a thermal insulator. A metal heating tip 102 is mounted in the tip 101 to extend from the distal end of the cable 22. The laser beam is delivered to the heating tip by the cable 22 to exit the distal end of the cable to strike the heating tip 102. The heating tip is made of a suitable material such as stainless steel which may be heated quickly to a high temperature and then used to cut and cauterize soft tissue in the mouth.

Other configurations of tips 92 which are interchangeable with the tips 92 or 92' shown in FIGS. 5 and 6 are also possible.

From the foregoing, it can be seen that the present invention provides a simple and yet highly effective dental laser system for removing carious lesions, enamel and soft tissue as well as sterilization and other dental procedures. The laser can also be used in endodontic applications for eradicating diseased nerve tissue as well as sterilizing the root canal. There are many advantages to the dental laser system of the present invention.

First, the dental laser system of the present invention is not only portable but it can also be operated from standard line current of 110 volts. As such, special electrical wiring is not required in order to utilize the dental laser system of the present invention.

A still further advantage of the dental laser system of the present invention is that the delivery system utilizes a handpiece dimensioned to simulate the conventional dental handpiece used by dentists. As such, the handpiece of the present invention can be easily maneuvered in the patient's mouth. Furthermore, the replaceable tips for the handpiece further enhance the flexibility of the operation and use of the dental laser of the present invention.

Having described our invention, many modifications thereto will become apparent to those skilled in the art to which it pertains without deviating from the spirit of the invention as defined by the scope of the appended claims.

We claim:

1. A method for creating an etch in the enamel in a tooth in a mouth, comprising the steps of:
    coating the tooth with a pigmented material over the enamel where this dental procedure is to be performed,
    aiming a pulsed laser so that the laser impinges upon the enamel,
    repeatedly activating the laser,
    wherein said laser has an energy output per pulse sufficient to cause microscopic holes in the enamel so that composites can be affixed to the enamel as a result of the adhesive agent entering these microscopic holes and causing a firm bond between the composite and the enamel,
    wherein said laser has an energy output of between 0.1 millijoules per pulse and 5 joules per pulse.

2. The invention as defined in claim 1 wherein the average power of said laser is between one tenth and fifty watts.

3. The invention as defined in claim 1 wherein the laser has a pulse repetition rate of between one and 10,000 pulses per second.

4. The invention as defined in claim 1 wherein said pulsed laser is a Nd:YAG laser.

5. The invention as defined in claim 1 wherein said laser is a Holmium doped laser.

6. The invention as defined in claim 1 wherein said laser is an Erbium doped laser.

7. A method for creating an etch in the enamel in a tooth in a mouth, comprising the steps of:
    aiming a pulsed laser so that the laser impinges upon the enamel,
    repeatedly activating the laser,
    wherein said laser has an energy output per pulse sufficient to cause microscopic holes in the enamel so that composites can be affixed to the enamel as a result of the adhesive agent entering these microscopic holes and causing a firm bond between the composite and the enamel,
    wherein said laser has an energy output of between 0.1 millijoules per pulse and 5 joules per pulse.

8. The invention as defined in claim 7 wherein the average power of said laser is between one tenth and fifty watts.

9. The invention as defined in claim 7 wherein the laser has a pulse repetition rate of between one and 10,000 pulses per second.

10. The invention as defined in claim 7 wherein said pulsed laser is a Nd:YAG laser.

11. The invention as defined in claim 7 wherein said laser is a Holmium doped laser.

12. The invention as defined in claim 7 wherein said laser is an Erbium doped laser.

* * * * *